(12) United States Patent
Peponnet (10) Patent No.: US 6,277,604 B1
(45) Date of Patent: Aug. 21, 2001

(54) METHODS FOR SOLID-PHASE NUCLEIC ACID AMPLIFICATION AND SEQUENCING

(75) Inventor: Christine Peponnet, Paris (FR)

(73) Assignee: Genset (FR)

( * ) Notice: Subject to any disclaimer, the term of this patent is extended or adjusted under 35 U.S.C. 154(b) by 0 days.

(21) Appl. No.: 09/430,035

(22) Filed: Oct. 29, 1999

Related U.S. Application Data (63) Continuation of application No. 08/836,031, filed as application No. PCT/FR95/01422 on Oct. 27, 1995.

(30) Foreign Application Priority Data

Oct. 28, 1994 (FR) .................................................. 94/12972

(51) Int. Cl.$^7$ .............................. C12Q 1/68; C12P 19/34; C07H 21/04
(52) U.S. Cl. ........................... 435/91.1; 435/6; 435/91.2; 536/24.3; 935/77
(58) Field of Search .................................. 435/91.2, 91.1, 435/6; 935/77; 536/24.3

(56) References Cited

U.S. PATENT DOCUMENTS

| 4,882,127 | 11/1989 | Rosenthal et al. ...................... 422/50 |
|---|---|---|
| 5,451,453 | 9/1995 | Gagnon et al. .................... 428/305.5 |

FOREIGN PATENT DOCUMENTS

| 480408 | 4/1992 | (EP) | ................. | C12Q/1/48 |
|---|---|---|---|---|
| 90 01546 | 2/1990 | (WO) | ............................ | C12N/15/00 |
| 91 00868 | 1/1991 | (WO) | ............................. | C07H/21/00 |
| 91 08307 | 6/1991 | (WO) | ............................... | C12Q/1/68 |
| 93 03052 | 2/1993 | (WO) | ............................ | C07H/21/02 |
| 93 04199 | 3/1993 | (WO) | ............................... | C12Q/1/68 |
| 93 09250 | 5/1993 | (WO) | ............................... | C12Q/1/68 |
| 93 13220 | 7/1993 | (WO) | ............................... | C12Q/1/68 |
| 93 15228 | 8/1993 | (WO) | ............................... | C12Q/1/68 |

OTHER PUBLICATIONS

McCabe, Production of single–stranded DNA by asymmetric PCR, PCR protocols: a guide to methods and applications. p. 76–83., 1990*

* cited by examiner

*Primary Examiner*—W. Gary Jones
*Assistant Examiner*—Joyce Tung
(74) *Attorney, Agent, or Firm*—Saliwanchik, Lloyd & Saliwanchik (57) ABSTRACT

Methods for amplifying and sequencing nucleic acids are disclosed. In addition, supports for the solid phase amplification or sequencing of nucleic acids are disclosed. The supports comprise a solid support, a linker arm having functional groups capable of binding to the solid support, and an oligonucleotide bound to the linker arm.

13 Claims, 6 Drawing Sheets

METHODS FOR SOLID-PHASE NUCLEIC ACID AMPLIFICATION AND SEQUENCING

This application is a continuation of U.S. patent application Ser. No. 08/836,031, filed on Jul. 11, 1997, which is a national stage application of PCT/FR95/01422 filed on Oct. 27, 1995, which is the PCT application from FR 94/12972, filed Oct. 28, 1994, each of which is hereby incorporated by reference in its entirety.

FIELD OF THE INVENTION

The present invention relates to a process for the solid-phase amplification of nucleic acids, as well as to a reagent kit which is useful for carrying out the process.

The present invention also relates to a process for immobilizing a primer on a solid phase.

BACKGROUND OF THE INVENTION

Amplification on a solid phase consists of the elongation, during a PCR reaction or other types of amplification, such as LCR, SDA, etc., of a primer which is prebound to a solid support. Such a technique makes it possible to obtain an amplification product one specific strand of which is covalently attached to the solid phase, without using any steps other than PCR. This makes it possible to carry out detection before denaturation on double-stranded DNA, or after denaturation on a specific strand of the amplification product by combining PCR and detection without changing support.

Methods for the solid-phase amplification of nucleic acids have been described in WO 89/11546, AU 47144/89 and WO 93/09250.

This type of amplification on a support may be very useful for all the molecular biology diagnostic applications, in particular for detecting infectious targets or genomic targets. This technique makes it possible to reduce detection times as well as the risks of errors, since the sample is not transferred from one well to another but the entire experiment takes place on the same support. Moreover, for all the applications requiring only a single specific DNA strand, such as cloning or sequencing, this technique may allow a real saving in time and great ease of use avoiding many intermediate steps.

The primer involved in the PCR, which is bound at its 5' end to the solid support, must form part of the strand which it is desired to elongate on the solid support. The 3' end of the primer must be free, unmodified and homologous with the target, in order to allow its elongation by a polymerase.

However, a major drawback of solid-phase amplification is the low yield of elongation on the solid phase.

SUMMARY OF THE INVENTION

In order to decrease the solid support/oligonucleotides steric interactions and to improve the accessibility of Taq polymerase to the hybrid formed by the bound primer and the complementary amplification product, a connecting or "linker" arm is placed at the 5' end of the bound primer. This linker arm is also referred to as a "spacer arm" since it serves to physically distance the 3' end of the bound primer from the solid support so as not to hinder the cooperation of the various amplification reagents with the primer.

It has been discovered, according to the present invention, that one of the parameters influencing the yield of elongation lies in the mode of binding of the primer to the solid support. The nucleotides of the primer themselves are liable to be involved in covalent bonding with the support under the coupling conditions used between the "linker" and the solid support, this contributing towards the low yield of elongation of the primer. More precisely, it has been discovered that, more than the size of the linker arm, it is the reactivity or the multiplicity of the potential binding sites of the linker arm on the support which increases the yield of elongation of the primer.

The subject of the present invention is a process for the solid-phase amplification of nucleic acids, in which a primer immobilized on a functionalized heat-resistant solid support is used, characterized in that the said primer is immobilized on the solid support by means of a covalent bond between the solid support and a functional group of a polyfunctional molecule, the said molecule itself being linked to the 5' end of the said primer.

More precisely, the said primer is immobilized on the solid support by means of a connecting (or "linker") arm which consists of a residue of the said poly-functional molecule placed between the solid support and the 5' end of the primer and establishing a covalent bond between a functional group of the solid support and a first functional group of the said polyfunctional molecule, on the one hand, and between the 5' end of the primer and a second functional group of the said poly-functional molecule, on the other hand.

By increasing the number of functional groups in the linker arm, the elongation yield is increased. It is thought that this is due to the fact that the probability is thereby increased that the binding to the solid support takes place by means of the linker arm, that is to say without the primer itself actually being involved.

DETAILED DESCRIPTION OF THE INVENTION

The expression functional group of the said polyfunctional molecule is understood here to refer to a group capable of establishing a covalent bond with the solid support. Amine, hydroxyl, carboxyl, aldehyde, thiol and phosphate groups are mentioned in particular as functional groups.

When the linker arm contains a very reactive group such as a terminal phosphate group at its end which is not linked to the primer, it is not necessary for the polyfunctional molecule to contain a large number of functional groups. However, the said polyfunctional molecule preferably contains at least five, more preferably at least ten, functional groups.

In an advantageous embodiment of the invention, the said polyfunctional molecule comprises a polymer fragment. Preferably, each monomer unit of the said polymer fragment contains at least one functional group. In this case, an increase in the size of the linker arm, that is to say the polymer, is reflected by an increase in the number of potential sites for terminal binding of the primer and allows the elongation yield to be increased, this being although the overall level of binding of the primer to the solid support remains constant.

Preferably, the polymer fragment added to the 5'end of the said primer contains more than 5 monomers, more preferably more than 10 monomers, in particular up to 50 monomers.

Advantageously, the said polymer fragment according to the invention comprises a homopolynucleotide fragment or a fragment of a polynucleotide analog.

The term "polynucleotide analog" is understood here to refer to a polymer whose monomer units are joined by a phosphodiester linkage similar to the phosphodiester linkage of natural polynucleotides. In other words, it is a polymer in which the nucleoside residues of the nucleotide monomers are replaced with non-nucleoside residues, in particular aliphatic residues. Mention is made in particular of the polymer fragments of formula (I) below:

(I)

in which R is an aliphatic residue, in particular of from 2 to 20 carbon atoms, such as an alkylene residue, R containing at least one functional group according to the invention, and n is an integer from 2 to 50 in particular.

Preferably, the polymer fragment of polynucleotide-analog type according to the invention contains several reactive groups grafted onto each monomer, in particular amine or hydroxyl groups, and in this case n may more particularly be between 2 and 10 only.

When the linker arm consists of a homopoly-nucleotide fragment, it preferably contains more than 5 nucleotides, more preferably more than 10 nucleotides, in particular up to 50 nucleotides.

The polynucleotide analogs according to the invention may be obtained by synthetic methods similar to the methods for synthesizing DNA, in particular by automated synthesis on a solid support. Indeed, these polymer fragments may be obtained by condensation of monomer synthons which are suited to the processes of nucleotide synthesis involving the use of phosphoramidite synthons, that is to say a synthon containing, in a conventional manner, two terminal OH groups, one of which is protected by a dimethoxytrityl (Dmtr) group and the other by a phosphoramidite group. The polymer fragment of polynucleotide-analog type corresponds in this case to the condensation of synthons similar to the standard nucleotide synthons in which the divalent nucleoside residue at 5' and 3' is replaced by an aliphatic residue, in particular an alkylene residue.

More particularly, in order to obtain the poly-nucleotide-analog polymer fragments of formula (I), it is possible to use phosphoramidite synthons of formula:

Thus, when the linker arm is a polynucleotide fragment or polynucleotide analog, the linker arm or the primer conjugated to the linker arm may advantageously be prepared directly by nucleotide-type synthesis, the said conjugate being subsequently coupled to the solid support according to the invention.

The polymer fragment, in particular homopoly-nucleotide or polynucleotide analog, may be a branched fragment, that is to say one containing several branches. This type of fragment may be obtained using a monomer which may serve as a base for condensation with several monomers on the same synthon. Mention is made in particular of the following phosphoramidite synthon (ref. 5250-1 from Clontech):

which may be used in the synthetic process of the automated DNA synthesis type and may condense with two monomers in parallel.

Advantageously, the said polymer and in particular the homopolynucleotide fragment or polynucleotide analog placed between the solid support and the primer contains, at its end which is not linked to the primer, a reactive terminal functional group which may establish a covalent bond with the solid support. A hydroxyl group or an amine and, more preferably, a phosphate group are mentioned in particular as the said reactive terminal functional group of the polymer fragment.

The use of a terminal phosphate group is particularly recommended when the linker arm is a poly-T. In the absence of phosphate group, a poly-A or poly-C linker arm is more effective.

The methods of automated DNA synthesis on a solid support make it possible chemically to phosphorylate the terminal 5' end of large amounts of oligonucleotides. It is therefore possible, by these methods, to prepare linker arms of homopolynucleotide type or polynucleotide-analog type or conjugates of these linker arms and of the primer, which are phosphorylated at the 5' end of the linker arm.

According to the invention, the solid support consists of functionalized organic or inorganic polymer.

According to the present invention, certain characteristics of the solid support are advantageous for being able to elongate an oligonucleotide primer bound to a solid support as a product of amplification. Firstly, this solid support must be heat-resistant, that is to say capable of withstanding the high temperatures of PCR (100° C.) and must be of good heat conductance. It must be functionalized, that is to say contain chemical functions, in order to allow the stable binding of an oligo-nucleotide primer to the solid support. This primer/solid support bonding must also withstand high temperatures.

This is why, according to the present invention, covalent bonding is preferred. The Taq polymerase or other enzyme responsible for the elongation should not be inhibited by the components of the support. Lastly, such a support should have optical properties which allow calorimetric or fluorescent detection with no background noise. A transparent support is preferred since it allows the use of reading equipment of any type.

Types of plastic which have great resistance to high temperatures are thus preferably used. Plastics based in particular on heat-resistant modified polystyrene, on styrene/acrylonitrile copolymer, on polycarbonate, on polypropylene or on glass are mentioned in particular.

Solid plastic supports functionalized by UV treatment in order to induce the appearance of $NH_2$ functional groups may be used (ref. 1). However, according to the present invention, the solid support may be a poly-functionalized support, that is to say one containing a multiplicity of functional groups, in particular aldehyde, carboxyl, amine, hydroxyl or thiol, which promote the establishment of a stable covalent bond with the linker arm consisting of the said polyfunctional molecule linked to the primer.

Plastic supports which have been treated by corona treatment or gamma-irradiation in order to induce the appearance of a multiplicity of functional groups are appropriately used. This type of treatment is simple and avoids the use of chemical reagents for functionalization.

Polycarbonate or a styrene/acrylonitrile copolymer which are functionalized, inter alia, by corona treatment or gamma-radiation are used in particular as preferred heat-resistant support.

Methods for the covalent bonding of oligo-nucleotides to solid supports functionalized by means of a terminal functional group of the oligonucleotide are known (ref. 1 to 5). However, according to the invention, the homopolynucleotide fragments may be bound to the solid support via the natural functional groups, in particular amine and hydroxyl of the nucleotide bases themselves, or via a terminal functional group, in particular phosphate.

Similarly, the fragments of polynucleotide-analog type may also be bound to the solid support via a terminal group or one of the functional groups, in particular amine or hydroxyl, which are substituted on the monomers.

This coupling between the functional groups of the linker arm, in particular of the homopolynucleotide fragment or polynucleotide analog, and the functional groups of the support may take place by chemical coupling in the presence of conventional activating agents. In particular, chemical coupling to a polyfunctional support is carried out in the presence of an activating agent of carbodiimide type, such as EDC.

The subject of the present invention is also a process for immobilizing a primer on a solid phase, this primer being useful in carrying out an amplification process according to the present invention, characterized in that covalent coupling is carried out between the said functionalized support and the said polyfunctional molecule linked to the 5' end of the said primer.

The solid support may be the inner surface of the PCR reaction container, or a solid component which is introduced into the container before the reaction, such as beads. The inner surfaces of microtitration microplate wells or of assay tubes are mentioned in particular as solid support.

The preferred format is the microplate format. The reason for this is that its widespread use and all the already-existing apparatus around this format allow it to be automated quickly and readily. Two types of microplate are commonly used. The first is of standard type with flat-bottomed cylindrical cupules. The second does not contain cylindrical cupules as above, but wells in the form of a small, flat-bottomed truncated tube. This form of tube allows ready adaptation to the thermal cycler and allows excellent thermal conductance.

The subject of the present invention is also a process for immobilizing a primer on a solid phase, this primer being useful in carrying out an amplification process according to the present invention, characterized in that covalent coupling is carried out between the said functionalized support and the said polyfunctional molecule linked to the 5' end of the said primer.

Solid-phase amplification allows amplification and detection to be carried out on the same support. The amplification product elongated on the solid surface may be detected in different ways. The double-strand bound to the support may be detected either by revealing a label incorporated during the PCR, in particular by means of a second labeled primer, or via the use of an ethidium bromide, YOYO, TOTO or POPO type intercalating agent (Molecular Probes Ref. 6 to 8). After denaturation, the single strand specifically bound to the solid support may also be detected by a labeled probe.

The detection consists, for example, in hybridizing a biotinylated oligonucleotide probe which specifically recognizes the amplification product elongated on the plate. A streptavidin/alkaline phosphatase conjugate recognizes the biotin species of the hybridized probe and, after dephosphorylation of a substrate, generates a calorimetric or fluorescent product.

The mode of binding of the primer according to the present invention is a determining factor for the elongation. This is because if the primer has a linker arm according to the invention, the elongation yield may be increased 15-fold depending on the type of arm, whereas the level of binding remains constant irrespective of the linker arm.

The amount of primer present in solution in the amplification reaction also plays an important role as regards the elongation yield. In order to have an optimum yield for elongation of the bound primer, an unequilibrated PCR is used (ref. 9). During the PCR, the primer bound to the solid support (primer A) is also present in solution but in lower amount, in particular 8 to 16 times less than the other amplification primer (primer X). The amplification takes place in two steps; the amplification is first exponential until the primer A in solution is depleted, the primers A bound to the solid support are next elongated, and the amplification then becomes arithmetic. The first step makes it possible to have a large number of copies and thus allows more effective elongation on the solid support. The amount of primer placed in solution is critical since it determines the moment at which the arithmetic amplification commences. An amount of about 5 to 10 pmol for the primer X and from 8 to 16 times less for the primer A gives good elongation yields.

The amplification process according to the present invention affords a real improvement when compared with the usual diagnostic techniques using PCR, be it for infectious or genetic diseases. Moreover, since the process according to the invention makes it possible to attach specifically a single strand to the solid phase, it may also be advantageous for sequencing, especially when large amounts need to be sequenced and when a simplification of the procedures and automation prove to be essential.

Other characteristics and advantages of the present invention will become apparent in the light of the detailed embodiment which follows.

Figure 1:
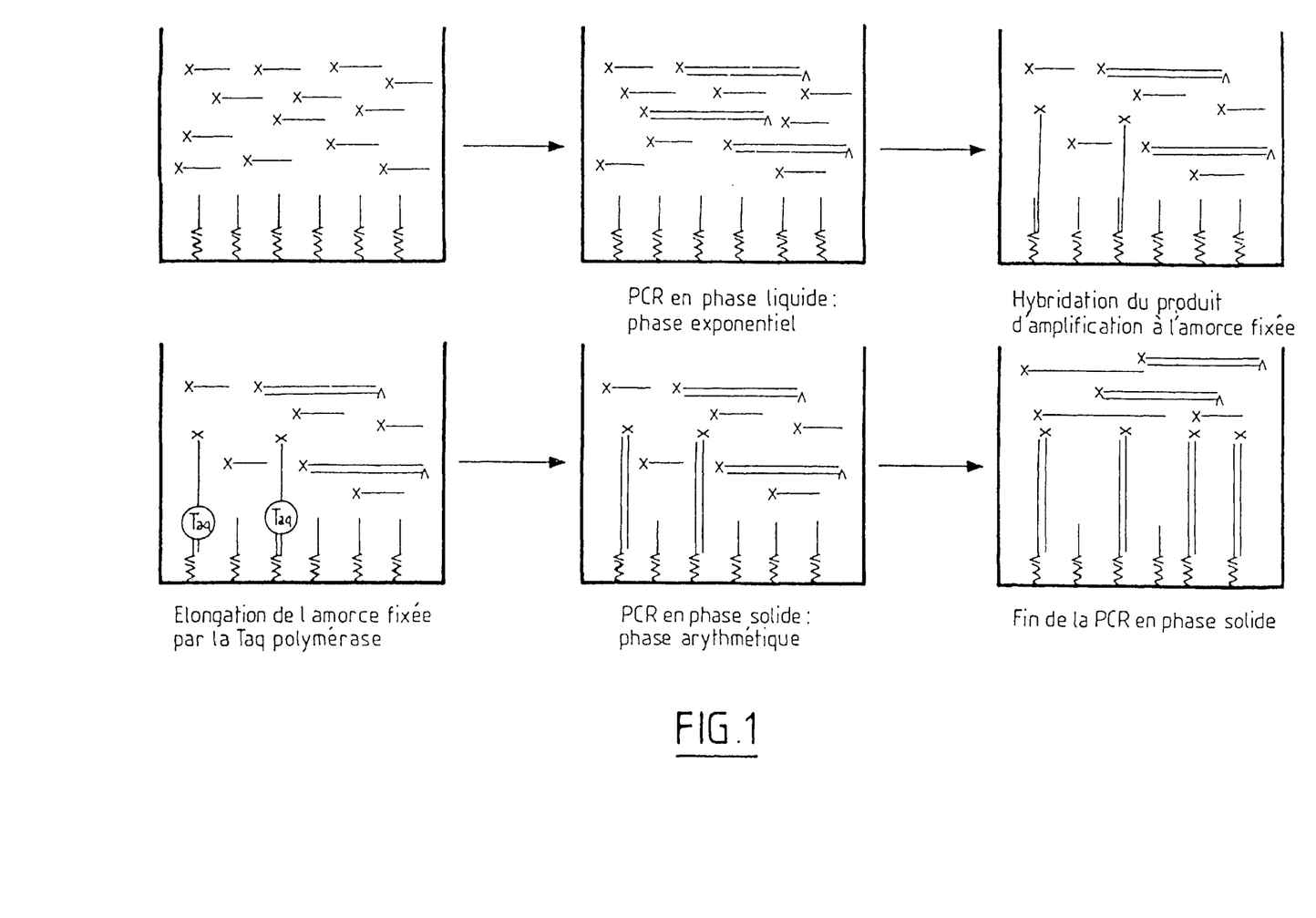
FIG. 1 represents, schematically, various steps of the solid-phase PCR

FIG. 1 represents the various steps in the solid-phase PCR.

| | |
|---|---|
| X———— | primer X in solution |
| A———— | primer A in solution |
| X======A | amplification product |
| vvvA—— | bound primer A |

Figure 2:
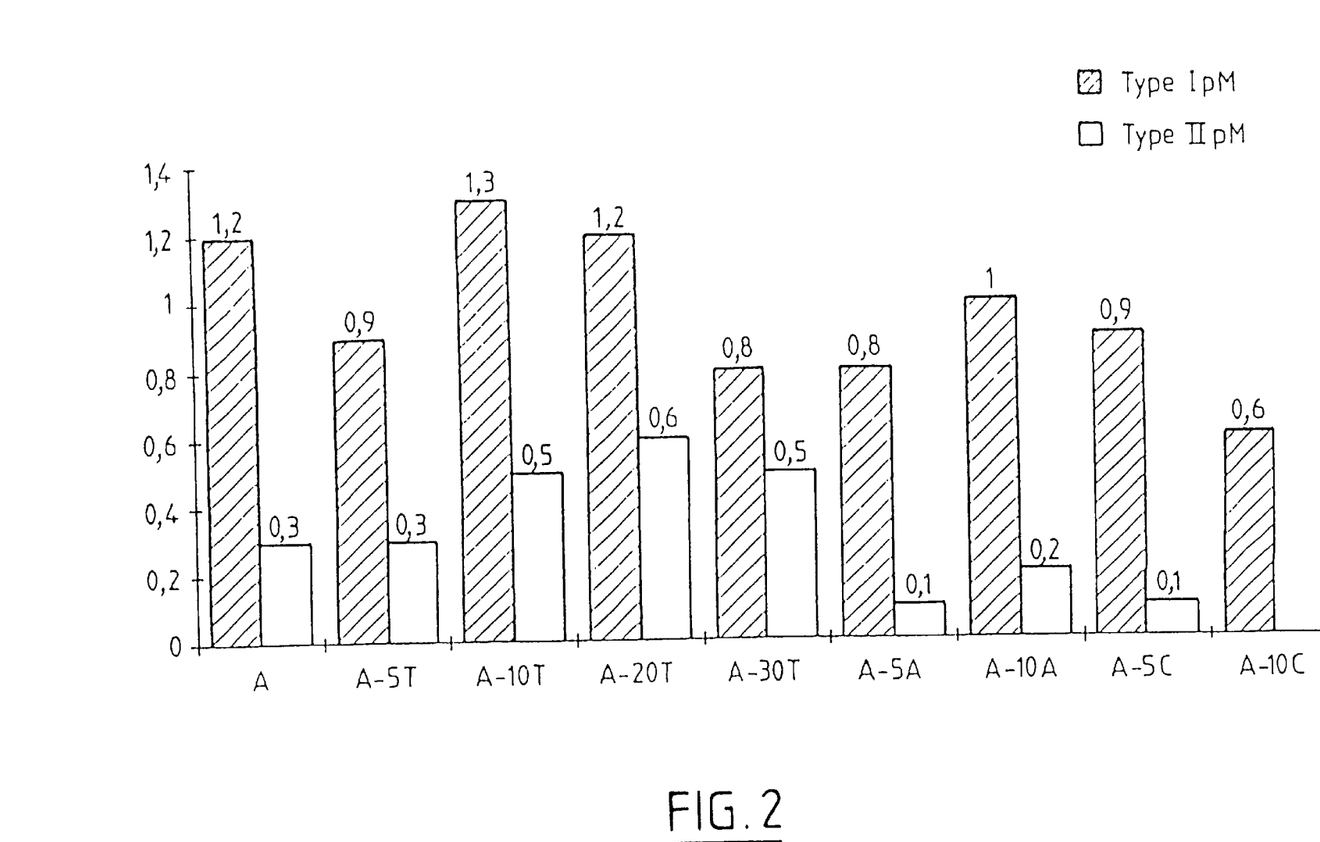
FIG. 2 represents primer-binding yield (pM) as a function of different linker arms.

FIG. 2 represents the binding yield in pM of the primer as a function of different linker arms.

Figure 3:
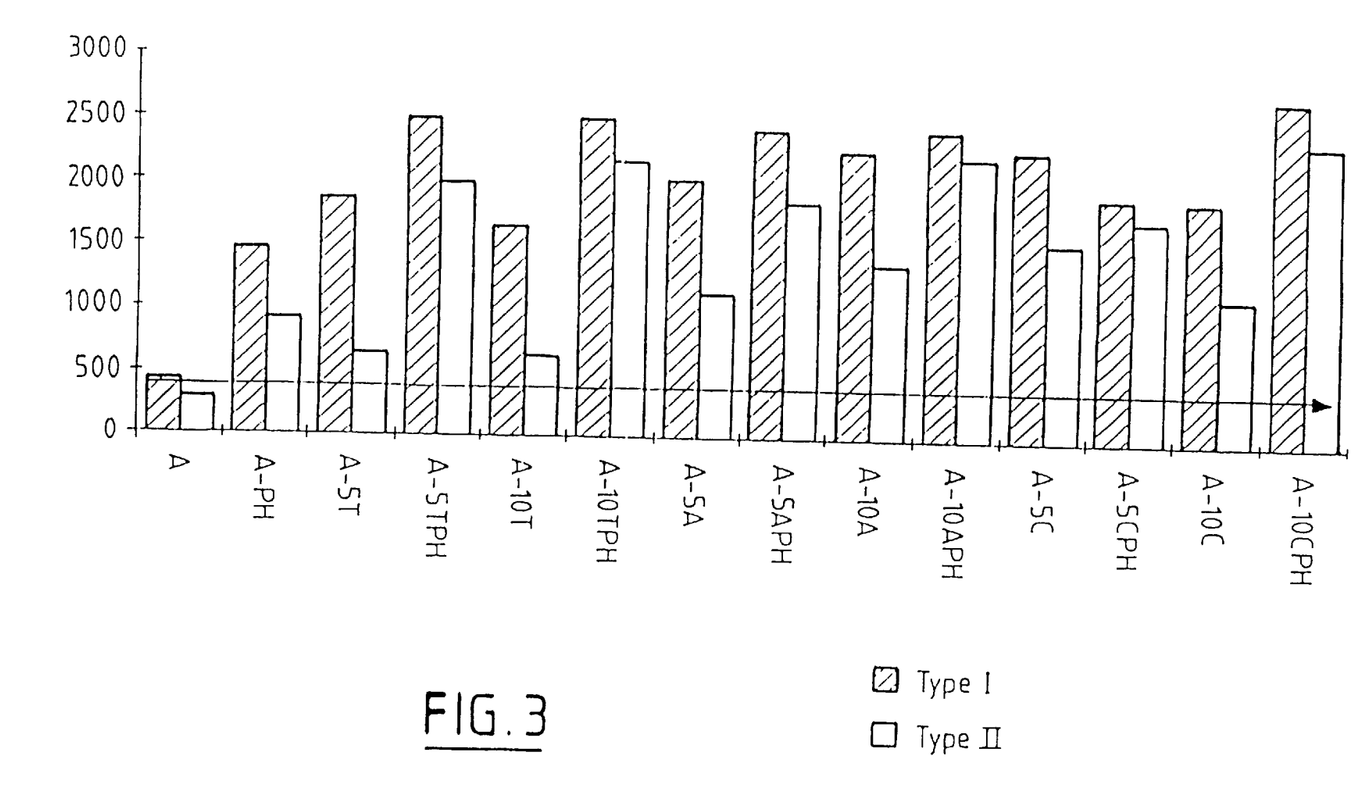
FIG. 3 represents the level of elongation (fluorescence units) as a function of different linker arms.

FIG. 3 represents the levels of elongation in fluorescence units as a function of different linker arms.

Figure 4:
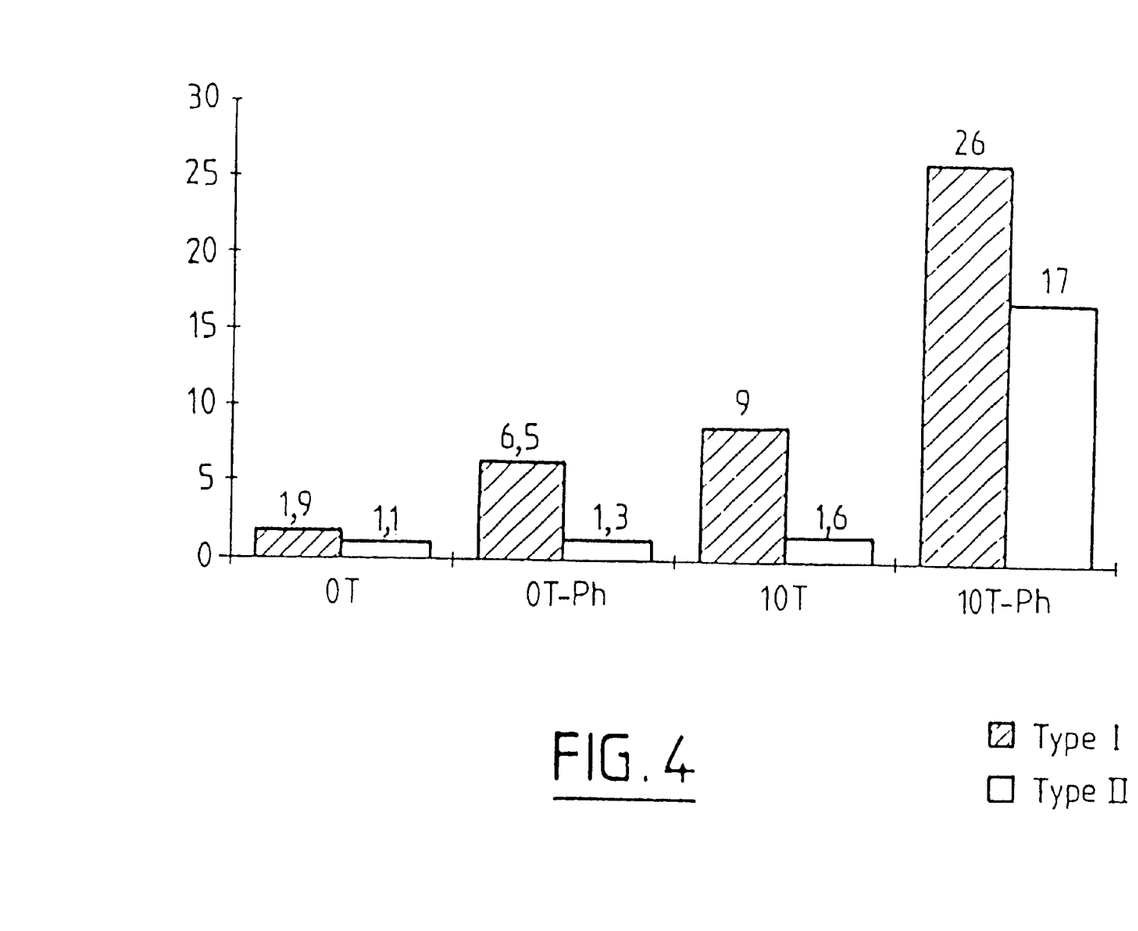
FIG. 4 represents the elongation yield (fMol of hybridized antiprobe).

FIG. 4 represents the elongation yield in fMol of hybridized antiprobe.

Figure 5:
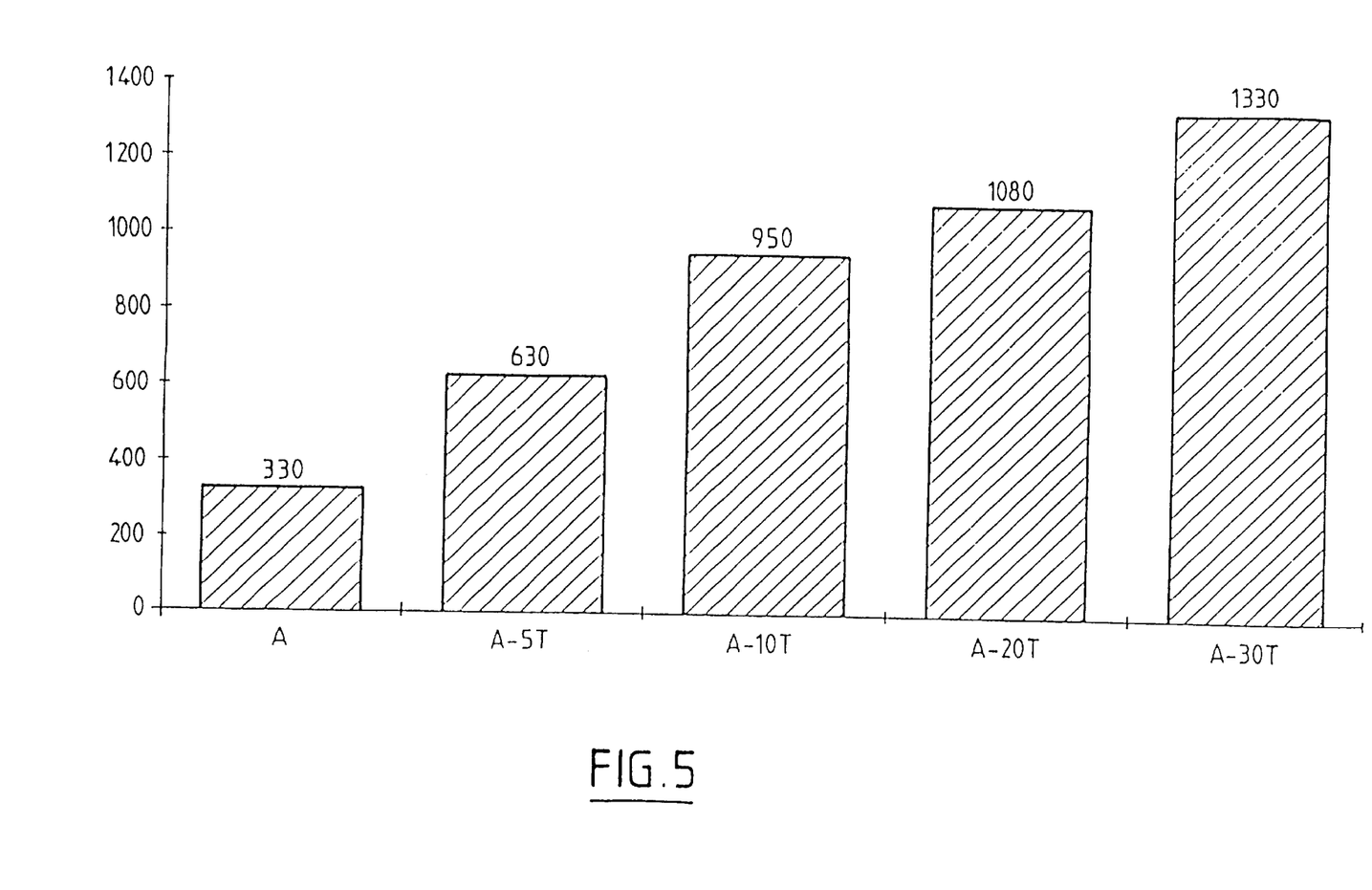
FIG. 5 represents the size of the linker arm on the level of elongation.

FIG. 5 represents the influence of the size of the linker arm on the level of elongation.

Figure 6:
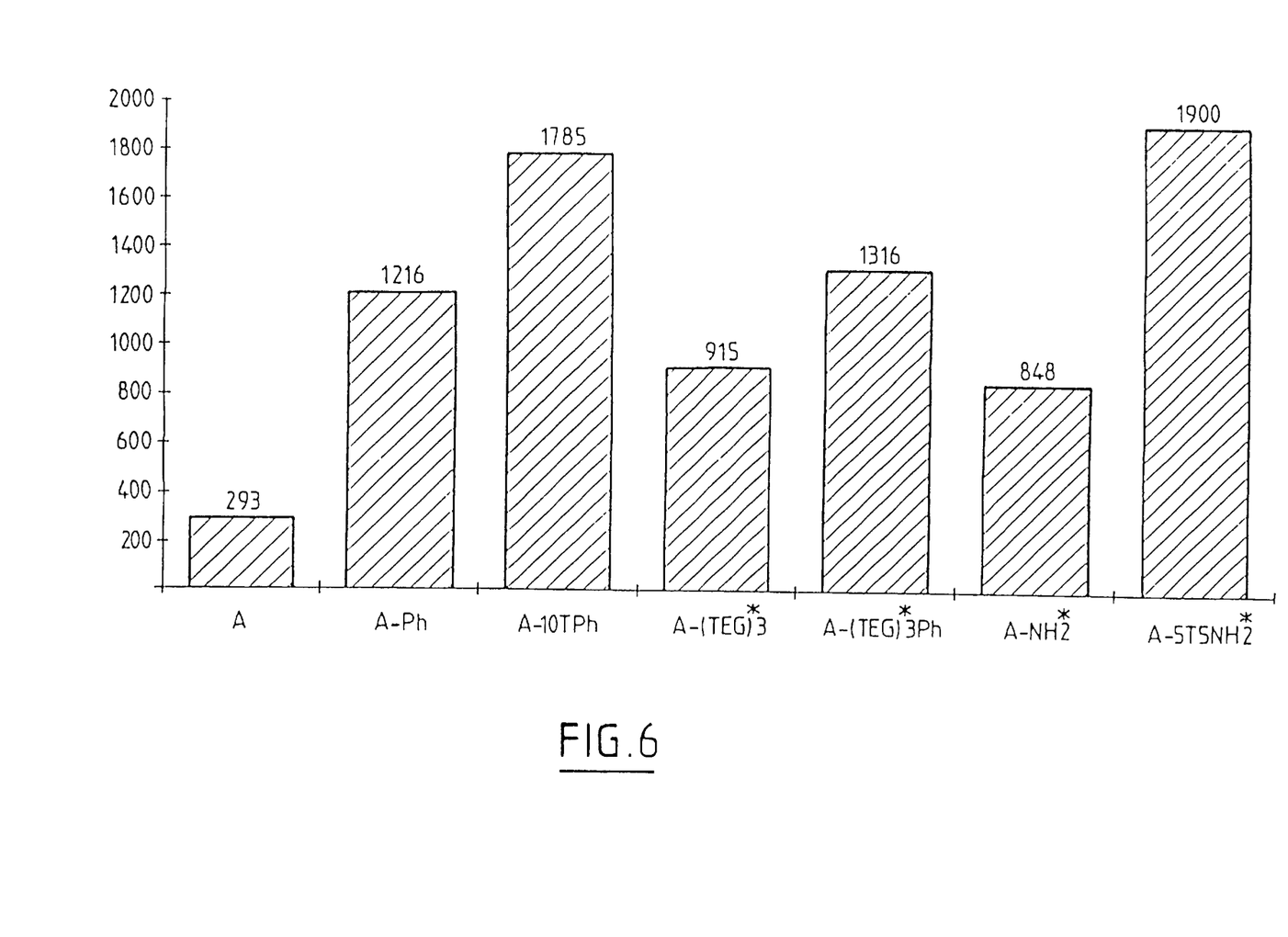
FIG. 6 represents the influence of various chemical functions of the linker arm on the level of elongation.

FIG. 6 represents the influence of various chemical functions of the linker arm on the level of elongation.

The process according to the invention was applied on an HLA-DRB model (ref. 10 and 11). M13 clones carrying a 280 bp insert corresponding to the amplification product were used as target. This HLA-DRB model made it possible to demonstrate the important parameters involved in the elongation and to study most particularly the problem of specificity of this technique.

1) Examples of different linker arms used.

| | | | |
|---|---|---|---|
| A, | A-Ph | | |
| A-5T, | A-10T | A-20T | A-30T |
| A-5T-Ph, | A-10T-Ph | | |
| A-5A, | A-10A | | |
| A-5A-Ph, | A-10A-Ph | | |
| A-5C, | A-10C | | |
| A-5C-Ph, | A-10C-Ph | | |

A = bound primer: CCCCACAGCACGTTTC(T,C)TG SEQ ID NO:1
Ph = terminal 5' phosphate group
xT, xA, xC = terminal 5'-position tail of x base T, of x base A or of x base C respectively.

A=bound primer: CCCCACAGCACGTTTC(T,C)TG SEQ ID NO: 1 Ph=terminal 5' phosphate group xT, xA, xC=terminal 5'-position tail of x base T, of x base A or of x base C respectively.

Linker arms comprising polymer fragments of the polynucleotide-analog type were also used (FIG. 6):

A —$N_2$*

A —5T −5 $NH_2$*

A —$(TEG)_3$*

A —$(TEG)_3$*Ph

The arm - $NH_2$* corresponds here to an aminoalkyl arm introduced via the Unilink® Amino Modifier synthon from Clontech, of formula:

The arm —5T −5 $NH_2$* corresponds to the successive condensation of 5 T nucleotides and then 5 Unilink® synthons in a phosphoramidite-type synthesis.

The condensation of Unilink® synthons led to a polynucleotide-analog fragment with alkylamine residues grafted onto the monomers.

—$(TEG)_3$* corresponds to the condensation of the synthon from Glen Research (ref: 10–1909 x) of formula:

—$(TEG)_3$* - Ph is obtained by 5'-terminal phosphorylation of the conjugate A —$(TEG)_3$* according to the phosphoramidite synthesis.

2) Solid support

Two types of polyfunctionalized heat-resistant support supplied by the company Nunc were used to evaluate the various linker arms. Type I is a heat-resistant modified polystyrene and type II is a styrene/acrylonitrile copolymer. They are in a microplate format and are cycled in a thermocycler supplied by Nunc.

These plastic supports were functionalized by a Corona treatment or gamma-irradiation, which consists conventionally in sending electric discharges into a chamber with controlled atmosphere and at fixed pressure. This functionalization allows the plastic support to be made capable of binding the oligonucleotide primers. This treatment causes functional groups of amine, alcohol, aldehyde, ketone, carboxylic acid, thiol, etc. type to appear at the surface of the plastic, these groups reacting chemically with the oligonucleotide to form a stable bond. Although very heat-resistant, the types of bonds formed are, however, at the present time poorly understood.

The chemical coupling is carried out in the presence of an activating agent according to the following procedure.

10 to 100 pmol of oligonucleotides are placed for binding per well in the presence of 10 to 50 mM final ethyl carbodiimide (EDC) and 10 to 50 mM final N-methylimidazole, pH 7, in a final volume of 100 µl. The plates are incubated for 5 to 15 hours at 50° C. and then washed 4 times with 0.4 N NaOH solution and 0.25% Tween 20, heated to 50° C.

3) Elongation of the primer on the solid phase

The elongation takes place in a final volume of 50 µl per well. 15 to 100 ng of the target DNA are amplified in a mixture comprising 1X PCR buffer II (Perkin Elmer), 0.25 mM $MgCl_2$ (Sigma), 200 µ$M_2$ dATP, dCTP, dGTP, dTTP (Pharmacia), 80 ng of primer X (CCGCTGCACTGTGAAGCTCT) SEQ ID NO: 2 and 10 ng of primer A with or without linker and 1.2 units of Taq polymerase (Perkin Elmer). The primer X is found in solution only, whereas the primer A is bound to the solid support and in solution. The amplification takes place on a thermocycler adapted to the microplate format, using the following method:

cycle 1:
5 min. at 94° C.
cycle 2 at 30:
30 sec. at 94° C.
30 sec. at 55°C.
30 sec. at 72° C.
cycle 31:
5 min. at 72° C.
4° C.

FIG. 1 represents the various steps of the solid-phase PCR. After amplification, the amplification products elongated on the solid phase are denatured. The wells are emptied and then washed 3 times with 0.4 M sodium hydroxide for 10 min.

4) Detection

Two types of detection were used. A semi-quantitative enzymic detection and a quantitative radioactive detection.

The enzymic detection is performed as described in the literature (9). In this method, after denaturation, 1 pM of biotinylated probe complementary to a region of the strand elongated on the solid support is hybridized.

The hybrid is revealed by a streptavidin/alkalyne phosphatase conjugate which converts a substrate into a chemiluminescent or fluorescent calorimetric product.

For the radioactive detection, a $^{32}$P-labeled probe is hybridized on the strand elongated on the solid support and the radioactivity is counted in a β counter.

5) Results

The binding capacity of the primer on the solid support was quantified by binding radioactively 5'-kinased primers and made it possible to show that the type I bound about 1 pM of primer per well, whereas the type II bound 0.2 pM.

FIG. 2 represents the binding capacity of the primer to two microplate supports as a function of the various types of linker arm. For a given type of support, the binding capacity does not vary significantly as a function of the arms used.

On the other hand, the elongation yield varies enormously as a function of the linker arm employed. The results are presented in FIGS. 3 and 5, which represent the levels of elongation of the supports as a function of the various arms used. The influence of the arm attached to the primer is a determining factor for the elongation yield, which may be increased 15-fold depending on the type of linker used, the level of binding remaining constant.

The poly-A and poly-C fragments are more effective than the poly-T fragments. Indeed, for linker arms of the same size, they give stronger signals for the elongation. The addition of a phosphate group always improves the elongation yield and this increase is more appreciable with the poly-T linker arm than with the poly-A or poly-C linker arms.

The elongation was quantified indirectly by hybridization of radioactive probes complementary to the part elongated by PCR. The level of hybridization was verified by hybridizing radioactive probes to wells containing a known amount of bound primers. The level of elongation varies according to the type of linker arm used, between 2 fM and 38 fM or between 1 fM and 17 fM for type I and type II respectively. These results are presented in FIG. 4.

The presence of several functional groups in the linker arm makes it possible to increase the level of elongation of the primer bound to the solid support. Thus, as shown in FIG. 6, a 45% increase is noted when 10 T is inserted between the primer and a terminal phosphate group. Similarly, the addition of a phosphate function to a (TEG)$_3$* linker arm makes it possible to increase the signal by 40% and 350% relative to the primer alone without linker arm. The same phenomenon is observed when a 5T5NH$_2$* arm is used; the level of elongation is increased by 110% relative to an NH$_2$* arm. The use of several different chemical functions thus makes it possible to promote the elongation of the primer on the solid phase by increasing the types of terminal linkages.

The amount of oligonucleotides elongated is, in fact, very low relative to the amount bound to the support. Despite this low amount, signal-to-noise ratios of about 30 are achieved with the enzymic detection technique described, which is entirely sufficient for a diagnostic application.

BIBLIOGRAPHY

1. "Covalent immobilization DNA onto Polystyrene microwells: the molecules are only bound at the 5' end". S. R. Rasmussen, et al. Anal. Biochem. 198, 138–142, (1991).

2. "A sensitive nonisotopic hybridization assay for HIV-1 DNA". G. H. KELLER, et al. Anal. Biochem. 177, 27–32 (1989).

3. "Immobilization of DNA via oligonucleotides containing an aldehyde or carboxylic acid group at the 5' terminus". J. N. Kremsky et al. Nucleic Acid Res. Vol. 15, Num. 7, 2891–2909, (1987).

4. "Detection of human immunodeficiency virus type 1 RNA in plasma from high risk pediatric patients by using the self sustained sequence replication reaction". C. E. Bush, J. Clin. Microbiol. 30, 281–286, (1992).

5. "Genetic analysis of amplified DNA with immobilized sequence-specific oligonucleotide probes". R. K. Saiki, et al. pNAS 86, 6230–6234 (1989).

6. "Use of the fluorescent dye YOYO-1 to quantifie oligonucleotides immobilized on plastic plates". M. Ogura, et al. Biotechniques 16, 1032 (1994).

7. "Stable dye-DNA intercalaton complexes as reagents for high-sensitivity fluorescent detection". A. N. Glazer, H. S. Rye, Nature 359, 859 (1992).

8. "Fluorometric assay using dimeric dyes for double- and single-stranded DNA and RNA with picogram sensitivity." H. S. Rye, et al. Anal. Biochem. 208, 144 (1993).

9. "Combined polymerase chain reaction-hybridization microplate assay used for detection of bovine leukemia virus and salmonella". S. R. Rasmussen, et al. Clin. Chem. 40: 200-5 (1994).

10. "Structure, sequence and polymorphism in the HLA-D region". J. Trowsdale, et al. Immuno. Rev., 1985, 85:5-43.

11. "ELA class II nucleotide sequences, 1992." J. G. Bodmer, Eur. J. Immunogen., 1993, 20:47-79.

What is claimed is:

1. A method for the solid-phase amplification of nucleic acids, which comprises contacting a support comprising a polyfunctionalized solid support;

a linker having a multiplicity of functional groups capable of binding to said solid support; and an oligonucleotide primer bound to said linker wherein said primer is immobilized on said solid support via said linker by means of at least one covalent bond between said functional groups and said solid support;

with a sample comprising at least one nucleic acid complementary to the primer bound to the solid support in the presence of a polymerase, and under reaction conditions which effect elongation of said primer.

2. The method according to claim 1, further comprising sequencing at least one nucleic acid sequence.

3. A method for the solid-phase amplification of nucleic acids, which comprises contacting a support comprising a polyfunctionalized solid support;

a linker having a multiplicity of functional groups capable of binding to said solid support; and a first oligonucleotide primer bound to said linker, wherein said primer is immobilized on said solid support via said linker by means of at least one covalent bond between said functional groups and said solid support;

with, in solution comprising at least one, nucleic acid complementary to the primer bound to the solid support in the presence of a polymerase, and a second amplification primer, under reaction conditions which effect elongation of said primer bound to the solid support and said second amplification primer, and amplification of said nucleic acid.

4. The method according to claim 3, wherein the primer bound to the solid support is also present in solution, but in a lower amount than said second amplification primer.

5. The method according to claim 3, wherein said second amplification primer is present in solution in an amount of about 5 to 10 pmol.

6. The method according to claim 4, wherein the amount of the primer bound to the solid support in solution is 8 to 16 times less than that of said second amplification primer.

7. The method according to claim 3, wherein said amplification occurs in a liquid phase, during which said amplification is exponential, until said second amplification primer is depleted, followed by amplification in a solid phase, during which amplification is linear.

8. The method according to claim 1, further comprising reacting an amplified nucleic acid with suitable reagents under appropriate conditions for the sequencing of at least one nucleotide.

9. The method according to claim 3, further comprising reacting an amplified nucleic acid with suitable reagents under appropriate conditions for the sequencing of at least one nucleotide.

10. A method for the solid-phase sequencing of nucleic acids, which comprises contacting a support comprising:

a poly solid support;

a linker having a multiplicity of functional groups capable of binding to said solid support; and an oligonucleotide primer bound to said linker wherein said primer is immobilized on said solid support by means of at least one covalent bond between said primer and said solid support;

with a sample comprising at least one nucleic acid complementary the primer bound to said support in the presence of suitable reagents, including a polymerase, and under appropriate reaction conditions for sequencing at least one nucleic acid sequence.

11. The method according to claim 1, wherein said solid support is heat resistant.

12. The method according to claim 1, wherein the linker is a polymer molecule.

13. The method according to claim 12, wherein the linker contains at least 5 monomer units.

* * * * *

UNITED STATES PATENT AND TRADEMARK OFFICE
CERTIFICATE OF CORRECTION

PATENT NO. : 6,277,604 B1
DATED : August 21, 2001
INVENTOR(S) : Christine Peponnet It is certified that error appears in the above-identified patent and that said Letters Patent is hereby corrected as shown below:

Column 3,
Line 9, "5'end" should read -- 5' end --.
Line 44, "homopoly-nucleotide" should read -- homopolynucleotide --.

Column 4,
Line 13, "homopoly-nucleotide" should read -- homopolynucleotide --.
Line 61, "oligo-nucleotide" should read -- oligonucleotide --.

Column 5,
Line 13, "poly-functionalized" should read -- polyfunctionalized --.
Line 26, "oligo-nucleotides" should read -- oligonucleotides --.

Column 10,
Line 42, "for detection" should read -- for the detection --.
Line 48, "ELA class" should read -- HLA class --.

Column 12, claim 10,
Line 33, "a poly solid support" should read -- a polyfunctionalized solid support --.
Line 42, "complementary the primer" should read -- complementary to the primer --.

Signed and Sealed this

Twelfth Day of March, 2002

Attest:

JAMES E. ROGAN
Attesting Officer
Director of the United States Patent and Trademark Office

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
ccccacagca cgtttcytg

```
-continued

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ccgctgcact gtgaagctct                                         20
```